United States Patent [19]

Denzer

[11] Patent Number: 5,333,621
[45] Date of Patent: Aug. 2, 1994

[54] CONDOM WITH TRANSDERMAL VASODILATOR

[76] Inventor: Eric Denzer, 34 Stiles Dr., Melville, N.Y. 11747

[21] Appl. No.: 69,976

[22] Filed: May 28, 1993

[51] Int. Cl.⁵ .......................... A61F 6/04; A61F 6/02
[52] U.S. Cl. .................... 128/844; 128/842; 128/918; 600/38
[58] Field of Search .............. 128/844, 842, 918; 604/304, 307, 890.1, 349; 424/449; 600/38

[56] References Cited

U.S. PATENT DOCUMENTS

| | | | |
|---|---|---|---|
| Re. 31,454 | 12/1983 | Hymes | 128/641 |
| 2,577,345 | 12/1951 | McEweb | 128/294 |
| 2,586,674 | 2/1952 | Lonne | 128/294 |
| 2,600,212 | 6/1952 | Dal Borgo | 25/156 |
| 3,136,417 | 6/1964 | Clinch | 206/63.2 |
| 3,339,546 | 9/1967 | Chen | 128/156 |
| 3,677,225 | 7/1972 | Czirely | 128/132 |
| 3,742,951 | 7/1973 | Zaffaroni | 604/304 |
| 3,759,253 | 9/1973 | Cray | 128/79 |
| 3,998,215 | 12/1975 | Anderson | 128/2.06 |
| 4,119,094 | 10/1978 | Misklus | 128/132 |
| 4,127,118 | 11/1978 | Latorre | 128/79 |
| 4,274,420 | 6/1981 | Hymes | 128/641 |
| 4,306,551 | 12/1981 | Hymes | 128/156 |
| 4,307,717 | 12/1981 | Hymes | 128/156 |
| 4,354,494 | 10/1982 | Hogin | 128/294 |
| 4,415,548 | 11/1983 | Reddy | 424/28 |
| 4,421,737 | 12/1983 | Ito et al. | 424/28 |
| 4,475,910 | 10/1984 | Conway | 604/352 |
| 4,638,043 | 1/1987 | Szycher et al. | 604/304 |
| 4,638,790 | 1/1987 | Conway | 128/132 |
| 4,640,688 | 2/1987 | Hauser | 604/352 |
| 4,675,009 | 6/1987 | Hymer et al. | 604/304 |
| 4,687,771 | 8/1987 | Gamble et al. | 514/253 |
| 4,704,282 | 11/1987 | Campbell et al. | 424/449 |
| 4,798,600 | 1/1989 | Meadows | 604/330 |
| 4,829,991 | 5/1989 | Boeck | 606/39 |
| 4,840,952 | 6/1989 | Gamble et al. | 514/253 |
| 4,849,226 | 7/1989 | Gale | 604/890.1 |
| 4,869,723 | 9/1989 | Harmon | 604/349 |
| 4,931,445 | 6/1990 | Goldstein et al. | 514/252 |
| 5,124,158 | 6/1992 | Ruwart | 424/449 |
| 5,137,032 | 8/1992 | Harmon | 128/844 |
| 5,147,855 | 9/1992 | Gozes et al. | 514/12 |
| 5,152,997 | 10/1992 | Ebert et al. | 424/449 |
| 5,177,070 | 1/1993 | Katz | 514/215 |
| 5,244,677 | 9/1993 | Kuckel et al. | 424/449 |

OTHER PUBLICATIONS

Blakeslee, "New Therapies are Helping Men to Overcome Impotence", Jun. 22, 1993, New York Times.

INFOTRACT computer printout of 14 newspaper and magazine articles summaries regarding transdermal patches.

Erickson, Deborah, "Skinside Out", *Scientific American*, vol. 256, Nov. 1991, pp. 128–130.

Clark, Matt et al. "Patching Up Drug Deliveries", *Newsweek*, vol. 107, Jun. 30, 1986, p. 69.

(List continued on the next page.)

*Primary Examiner*—Robert A. Hafer
*Assistant Examiner*—Michael O'Neill
*Attorney, Agent, or Firm*—Alfred M. Walker

[57] ABSTRACT

A condom with a vasodilator delivery system is provided for producing and maintaining the erection of a male penis during intercourse. The vasodilator may be applied as a coating in a suitable pharmaceutical vehicle to the inner surface of the condom during manufacture. Alternatively, the vasodilator may be contained in a transdermal patch adhered during manufacture to the condom inside wall. The transdermal patch comprises a thin, smooth-edged layered structure for dispensing a suitable vasodilator to the penis skin surface. The transdermal patch may remain attached to the condom inner wall during use, and in so doing release its vasodilator into a suitable vehicle and lubricant for spreading to the entire penis skin surface. Alternatively, the transdermal patch may have an inner and an outer adhesive so that, when manufactured, the patch adheres to the inner condom wall, but upon use, the user applies pressure to the outside condom surface adjacent to the patch to adhere the inner surface of the patch to the skin of the penis during use of the condom.

6 Claims, 2 Drawing Sheets

OTHER PUBLICATIONS

Woolley, Suzanne, "Helping the Medicine Down—Or In", *Business Week*, Jan. 22, 1990, p. 84.

"Habitrol" (nicotine transdermal system)—Physicians Desk Reference, 1993 Supplement, of Basel Pharmaceuticals, CIBA-GEIGY, Corp., Summit, N.J. 07901, pp. 675-679.

"P apaverine Hydrochloride (injection USP)—Physicians Desk Reference", 1993 Supplement, Eli Lilly & Co., Indianapolis, Ind. 46285, pp. 1328-1329.

"Papaverine-Intracavernosal" text excerpt, *Complete Drug Reference*, 1992 United States Pharmacopeia, Consumer Reports Books, Yonkers, N.Y. pp. 1032-1033.

"Papaverine-Dosage and Usage Information", text excerpt, *Complete Guide to Prescription Drugs*, The Body Press, Putnam Publishing Group, pp. 654-655

CONDOM WITH TRANSDERMAL VASODILATOR

BACKGROUND OF THE INVENTION

The present invention relates to providing the ability to engage in sexual intercourse for males having difficulty developing or maintaining penile erection. It is medically well known that there are many causes of male impotence, but that one potential solution to the problem of impotence is to provide dilation of the blood vessels of the penis in order to provide an erection.

Consequently, a reliable method of providing penile vasodilation is needed. It is well known that there are a number of pharmaceutically active vasodilator materials. One of them, papaverine hydrochloride, is known to be used for injection into the penis to produce erections.

Vasodilators thus being known for clinically producing erections, there remains to be developed a system of delivery of an effective vasodilator, such as papaverine, without the need for an injection. A system of drug delivery which has become known is the use of transdermal patches to deliver pharmaceutical materials percutaneously.

Such transdermal patches are known for assisting users to quit smoking, as with NICODERM ® of Marion Merrell Dow Inc. of Kansas City, Mo. 64114 or HABITROL ® of Basel Pharmaceuticals, Division of Ciba-Geigy Corp., Summit, N.J. 07901. NICODERM ® is a nicotine transdermal system in which the user attaches a medication-containing patch to the skin for varying time periods over several weeks. The patches comprising the system contain medication in varying doses. HABITROL ® includes a patch having an adhesive layer attached to a patch having an imbedded pad soaked with a solution of nicotine.

U.S. Pat. No. 5,124,158 of Ruwart describes transdermal antisecretory agents for gastrointestinal disease.

Such transdermal patches have advantages over oral administration of medications, in that the transdermal medication is not interfered with by gastric acids or enzymes, nor does the liver have the ability to interfere during the effective period of drug administration. Transdermal patches are generally layered structures, with the bottom-most, skin-facing layer comprised of an adhesive having microholes. Above this adhesive layer is a medication-containing layer, and a waterproof cover layer is generally provided. The adhesive serves to attach the patch to the skin and the medication in the central layer is provided to the skin through the microholes in the adhesive layer. The medication enters the bloodstream by percutaneous absorption, or, in common parlance, transdermal penetration. A further advantage of the patches is that, to an important extent, they reduce or eliminate user mistakes and forgetfulness. In addition, transdermal patches provide slow-release, measured medication over a period of time much longer than would be available if similar medication were taken orally.

Transdermal patches have been discussed for use with cancer patients ("Skin Patch Fights Cancer's Agony", *USA Today*, V. 120, p. 14–15, February 1992) to treat diabetics ("Skinside Out", by Deborah Erickson, *Scientific American*, V. 265, p. 128+, November, 1991) for cardiac patients ("Helping The Medicine Go Down- Or In", by Suzanne Wooley, *Business Week*, p. 84, Jan. 22, 1990; L. Gourse, "Patchwork Medicine", *Science 85*, V. 6, P. 79+, October 1985; Kaplan, G. "This Won't Hurt-Really", *Nation's Business*, V. 73, p. 25, August 1985) and to treat hormonal symptoms ("The Anti-Aging Patch for Women" *Good Housekeeping*, by S. Fields et al., V. 208, p. 163–164, February 1989; "Patching Up Your Health", *Prevention*, by Heidi Rodale, (Emmaus, Pa.) V. 40, p. 76–81, January 1988; "Hot Flash!", P. McCarthy, *Health*, (New York, N.Y.) V. 19, p. 29, November 1987; "More About Estrogen Skin Patches", *Saturday Evening Post*, (C. Servaas) V. 259, p. 52–54, Jan./Feb. 1987, *Newsweek*, V. 107, p. 69, Jun. 30, 1986), and transdermal patches have even been discussed for use in administering cosmetics and perfume. (Corie Brown, "From Making Hearts to Winning Them", *Business Week*, p. 153+, Nov. 16, 1987).

In "New Way to Take Medicine", *Good Housekeeping*, V. 203, p. 191, August 1986, author Harriet Manley discusses the mechanism by which medication flows from the patch to the skin.

Other literature discussing transdermal patches includes "Patching Up Drug Deliveries", *Newsweek*, V 107, P. 69, Jun. 30, 1986, by M. Clark and "New Technology Allows Medicine Without Pills", *Jet*, V. 69, p. 20, Jan. 20, 1986.

Nowhere in the prior art has there been a combination of a vasodilator and a transdermal patch for providing male erections. With this new and useful combination of elements, a third natural element in producing male erections for sexual intercourse is the well known use of condoms. Condoms are increasingly important in preventing the spread of sexually transmitted diseases, and, with the present invention, they will serve to provide enhanced, hygienic and safe sexual activity for men who otherwise are unable to have sex.

U.S. Pat. No. 2,577,345 of McEwen discloses a prophylactic condom having a reinforced cap to prevent breakage of the condom at the tip of the condom. U.S. Pat. No. 2,586,674 of Lonne discloses a prophylactic condom with reinforced annular extensions for structural integrity of the condom.

U.S. Pat. No. 3,136,417 of Clinch discloses a method of treating the surface of a condom with a lubrication oil deposited upon the surface of the condom. U.S. Pat. No. 2,600,212 of Dal Borgo describes a method of layer upon a surface with the application of heat. U.S. Pat. No. 3,339,546 of Chem discloses a patch bandage in general. U.S. Pat. No. 3,677,225 of Czirely describes a shortened condom which is adhesively attached to the skin.

U.S. Pat. No. 3,998,215 of Anderson discloses a hydrogel pad attachable to the skin for electro stimulation treatment of injured body limbs. U.S. Pat. No. 4,119,094 of Micklus describes a condom which is coated for a low coefficient of friction. U.S. Pat. Nos. 4,274,420, reissue 31,454, 4,306,551 and 4,307,717 of Hymes disclose substrate pads for attaching to the skin as electrodes or bandages. U.S. Pat. No. 4,354,494 of Hogin discloses a condom with an annular ring strap to hold the condom in place.

U.S. Pat. No. 4,475,910 of Conway describes a condom catheter having an adhesive to prevent leakage during urinary medical tests. U.S. Pat. No. 4,638,790, also of Conway describes a condom having an adhesive to maintain the condom in place. U.S. Pat. No 4,415,548 of Reddy discloses a condom saturated with a spermacide solution. U.S. Pat. No. 4,640,688 of Hauser describing a urinary catheter with a pressure adhesive. U.S.

Pat. No. 4,798,600 of Meadows discloses a condom with structural parts.

U.S. Pat. No. 4,869,723 of Harmon describes a condom with adhesive to hold the condom in place. Furthermore, U.S. Pat. No. 5,137,032 also of Harmon discloses a condom with adhesives to hold the condom in place.

Moreover, U.S. Pat. No. 5,137,032 of Harmon describes a condom having internally sprayed spermacide medicine, and auxiliary texturized portions to increase stimulation, but does not suggest the use of a transdermal patch within a condom, wherein the transdermal patch emits a vasodilator directly to the skin. Furthermore, nowhere in the prior art is there discussed the use of discreetly obscuring the view of a vasodilator patch for male erections, by secreting the patch within the condom, out of view from a sex partner.

SUMMARY OF THE INVENTION

The present invention combines a conventional condom with a vasodilator pharmaceutical material for generating and maintaining the erection of the penis for sexual intercourse. Delivery of the vasodilator to the penis is accomplished essentially through percutaneous absorption. In one embodiment the condom is provided with an inside coat of a lubricant and vehicle material which contains a vasodilator. In second embodiment, the vasodilator is provided within a three-layered transdermal patch which is adhered inside the condom during manufacture. The three-layered condom is provided with adhesives on its outer side, which faces and adheres to the condom inner wall, and upon its inner sides which faces and adheres to the skin of the penis during use.

In this second embodiment, there is an adhesive system employing adhesives of different strengths for selective release. The adhesive securing the transdermal patch to the condom wall is made releasable, and thus weaker, whereas the adhesive securing the patch to the penis skin is made stronger. When used, the condom wall adhesive releases, while the penis skin adhesive remains effective. The transdermal patch is thereby transferred from the condom wall to adhesive contact with the skin of the user's penis.

This selective adhesive system herein described can be user controlled or can function automatically. Where user control is desired, the stronger penis skin adhesive upon the inner surface of the transdermal patch is made pressure sensitive. The user applies manual pressure upon the outside wall of the condom adjacent to the position of the transdermal patch which is inside the condom. The user will know the location of the patch because a suitable visual indicator is provided on the outside wall of the condom adjacent to the location of the patch.

The manual pressure activates the penis skin adhesive, thereby adhering the transdermal patch to the penis. The weaker, releasable adhesive securing the patch to the condom wall will thereupon release, allowing the patch to remain on the penis and to move relative to the inside wall of the condom along with the penis.

In the alternative, if it is desired to have the penis skin adhesive function automatically to adhere the patch to the penis, the penis skin adhesive is provided in a form which adheres when the condom is placed upon the penis by the user, without the need to use additional manual pressure to activate the penis skin adhesive.

In this second embodiment, the vasodilator is stored and contained in the second, middle layer of the transdermal patch, which functions conventionally in the manner of transdermal medication patches to deliver the vasodilator to the penis skin surface when the patch is adhered to the skin of the user.

Also in this second embodiment, the patch itself is suitably thin and flexible, so as to be able to fit comfortably within the condom. In addition, the patch has at least one edge, since it is wafer-like in contour and may be manufactured as a disk, a square, or any useful shape for a medicinal patch. The patch is provided with a taper in its thickness, so that while its thickness is not great, the thickness is nonetheless tapered toward the at least one edge. The at least one edge is further made smooth. The tapering and smoothness of the at least one edge ensures a substantial absence of friction and mechanical obstruction when the patch moves relative to an adjacent surface.

The surfaces which will be adjacent to the patch, of course, are (a) the condom wall; and (b) the skin of the penis. In this second embodiment, the transdermal patch is transferred from the condom wall to the skin of the user's penis by the system of differential adhesives described above. Therefore, in this second embodiment, the surface adjacent to the patch, relative to which the patch must move, is the inner wall of the condom. The above-described thickness taper and smoothness of the at least one edge prevent mechanical tearing of the condom wall due to the relative motion of the patch and the condom wall.

In a third embodiment, the transdermal patch has two layers, with an adhesive only on the outer surface of the patch adjacent to the condom wall. In this embodiment, the patch remains attached to the condom wall during use. The inner surface of the patch, as well as the entire inner surface of the condom is provided with a lubricating pharmaceutical vehicle. The vasodilator is stored and contained in the inner surface of the patch.

When the condom of the third embodiment is placed in use, the inner layer of the transdermal patch releases vasodilator material, which mixes with and is spread by the lubricating pharmaceutical vehicle.

In addition to the foregoing considerations, the vasodilator of the third embodiment of the present invention is preferably user controlled. The two-layered transdermal patch of the third embodiment may be made pressure sensitive such that the user must apply manual pressure upon the outside of the condom adjacent to the patch in order to mechanically force the vasodilator from its stored position in the inner layer of the patch into contact with the vehicle/lubricant. In this pressure-sensitive embodiment the vasodilator is stored in isolation from the vehicle/lubricant. The vasodilator only will come into contact with the vehicle/lubricant when the user deliberately applies pressure as described above. As in the second embodiment, a suitable visual indicator would be provided so that the user would know the location of the patch inside of the condom.

A preferable alternative to a disk, square or other shaped of patch in both the second and third embodiments to construct the transdermal patch as an annular ring disposed within the condom.

With respect to motion of the patch relative to an adjacent surface in the third embodiment, the two-layered patch of the third embodiment remains adhesively attached to the condom inner wall during use. Thus, the patch of the third embodiment moves relative to the penis skin in use, since the penis skin would normally be expected to move relative to any condom wall during convention use of a condom. As with the second embodiment, the thickness tapering of the transdermal patch and the smoothness of its at least one edge provide for a substantial absence of friction and mechanical interference when the patch moves relative to an adjacent surface.

OBJECTS OF THE INVENTION

It is an object of the present invention to provide a system for conveniently and comfortably providing a male with an erection for sexual intercourse.

It is a further object of the invention to provide a vasodilator material in a combined transdermal patch and condom.

It is an object of the present invention to provide a vasodilator in combination with a condom.

It is an object of the present invention to provide a user-controlled penile transdermal patch where the user applies manual pressure to release the vasodilator material.

It is a further object of the present invention to provide a discreet transdermal patch within the interior of a condom, out of view.

It is an object of the present invention to provide a user-controlled penile transdermal patch where the user applies manual pressure to engage penis skin adhesive and thereby to control the attachment of the transdermal patch to the penis.

Other and further objects of the invention will become apparent as the invention is more fully explained. The foregoing list is provided merely as a series of examples, and is not intended to be exclusive or exhaustive.

DETAILED DESCRIPTION OF THE DRAWINGS

Figure 1:
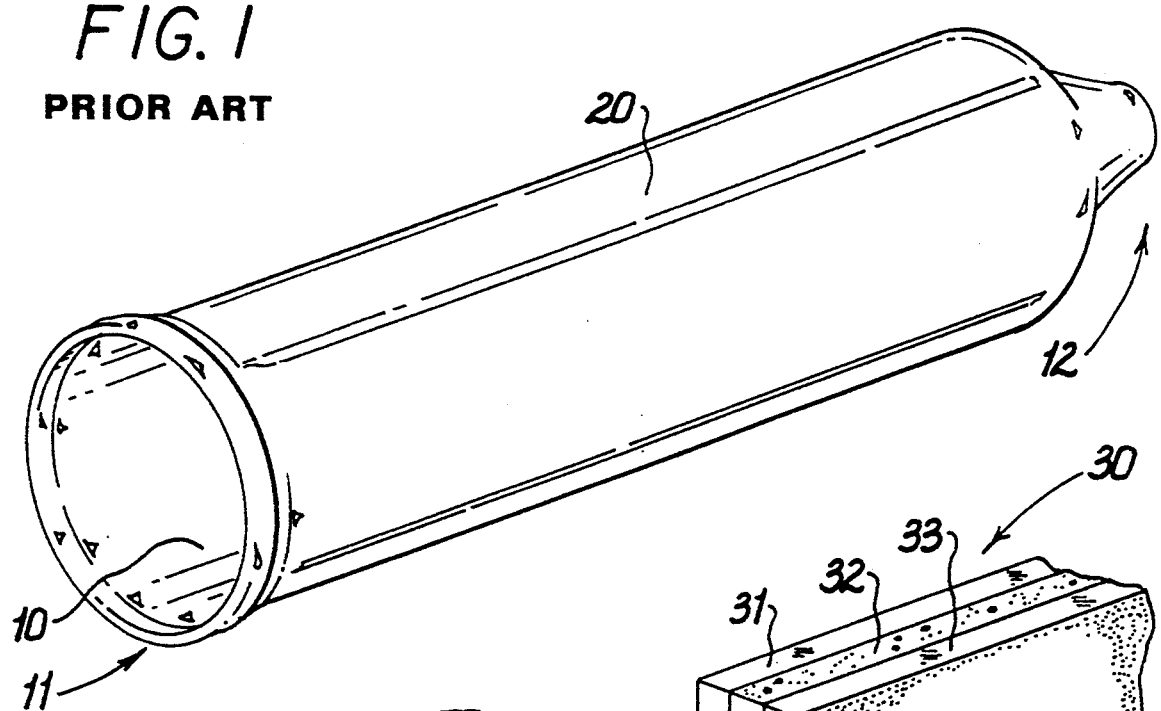
FIG. 1 is a perspective view of a prior art condom.

The drawings are described in the following manner, which all reference numerals being consistently used throughout the drawings.

FIG. 1 is a perspective view of a conventional condom, having an inside surface 10, an outside surface 20, an open end 11 and a closed end 12.

Figure 2:
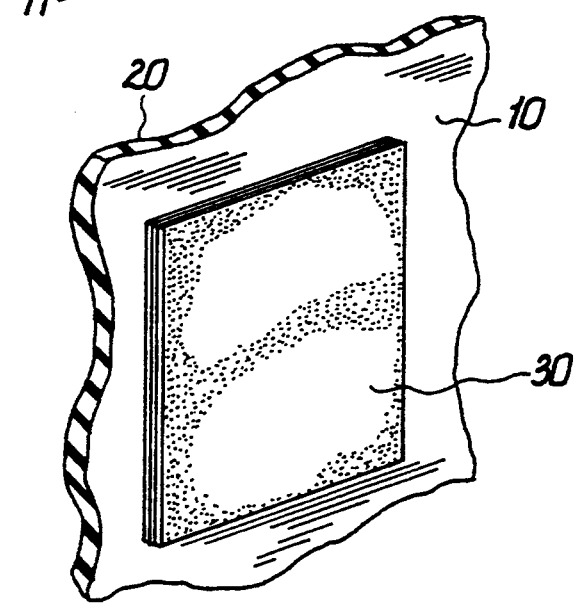
FIG. 2 is a cut away sectional view of the present invention.

FIG. 2 is a cut away sectional view of the inside surface 10 of a conventional condom on which is adhesively mounted three-layered transdermal patch 30, which is shown generally square in shape. The shape is of the transdermal patch is not critical.

Figure 3:
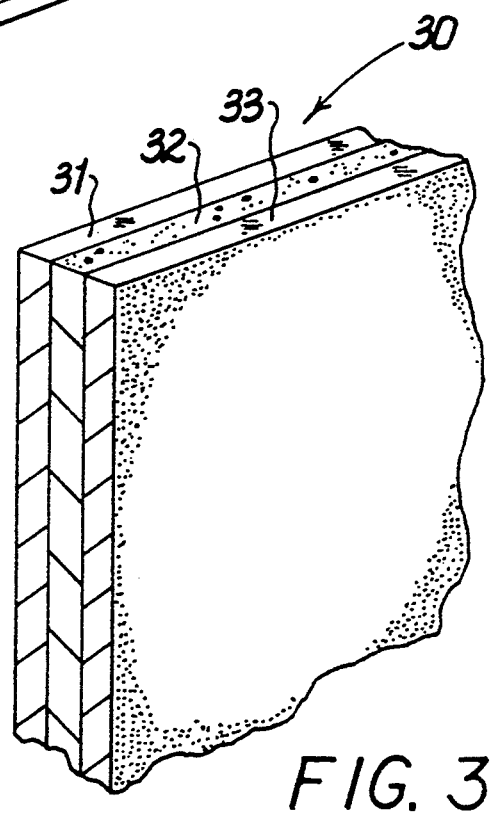
FIG. 3 is a perspective cross-sectional view of the present invention, as in FIG. 2.

FIG. 3 is a perspective cross-sectional view of 3-layered transdermal patch 30, having an outer adhesive layer 31 for adhering to the inside surface 10 of a condom; patch 30 is provided with middle layer 32 in which is contained and stored a vasodilator material for transdermal application to the penis; and patch 30 is provided with adhesive inner layer 33 for adhering to the skin of the penis.

Figure 3A:
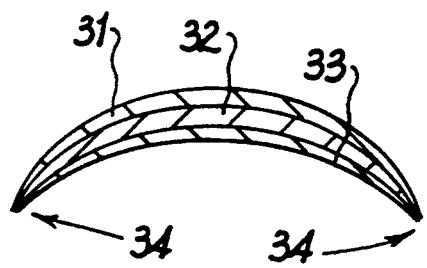
FIG. 3a is a curved, cross-sectional view of the present invention as shown in FIG. 2.

FIG. 3a shows a curved cross-sectional view of 3-layer patch 30, showing the detail of the tapered thickness. Layers 31, 32, and 33 are shown tapering to edges 34, which are smooth and substantially frictionless when subjected to motion relative to an adjacent surface.

Figure 4:
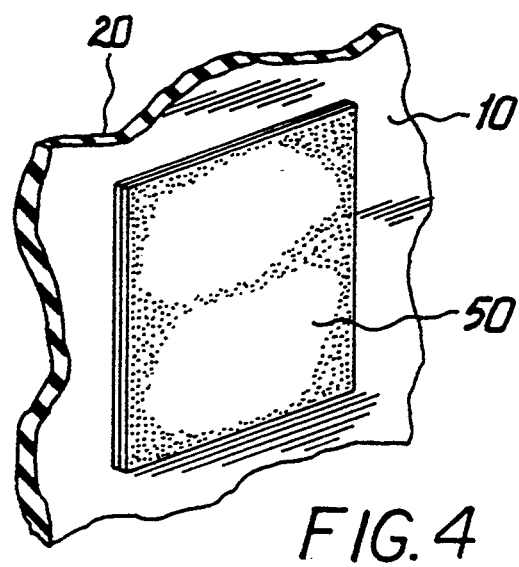
FIG. 4 is a perspective view of another embodiment of the present invention.

FIG. 4 shows a cut away perspective view of a 2-layered transdermal patch 50 adhesively disposed upon the inside surface 10 of a conventional condom.

Figure 5:
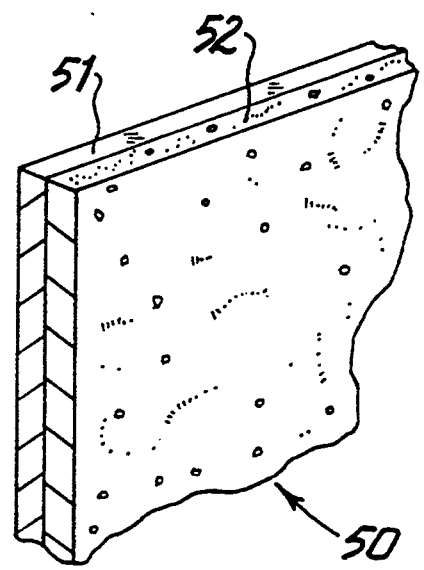
FIG. 5 is a cross sectional perspective view of the embodiment shown in FIG. 4.

FIG. 5 shows a cross sectional perspective of two-layered transdermal patch 50, having outer adhesive layer 51 which is adhered to the inside surface 10 of a conventional condom, and inner layer 52 containing and storing a vasodilator material for transdermal application to the skin of a penis.

Figure 6:
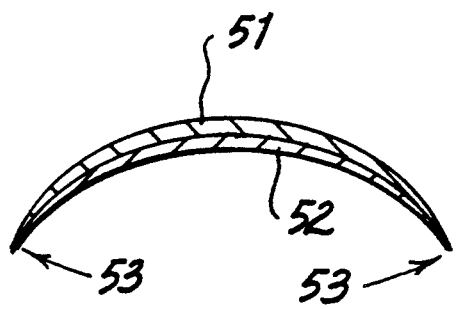
FIG. 6 is a cross sectional view of the embodiment shown in FIG. 4.

FIG. 6 shows a cross-sectional view of 2-layered transdermal patch 50 showing the thickness tapering, with layers 51 and 52 tapering to edges 53, which are smooth and substantially frictionless when subjected to motion relative to an adjacent surface.

Figure 7:
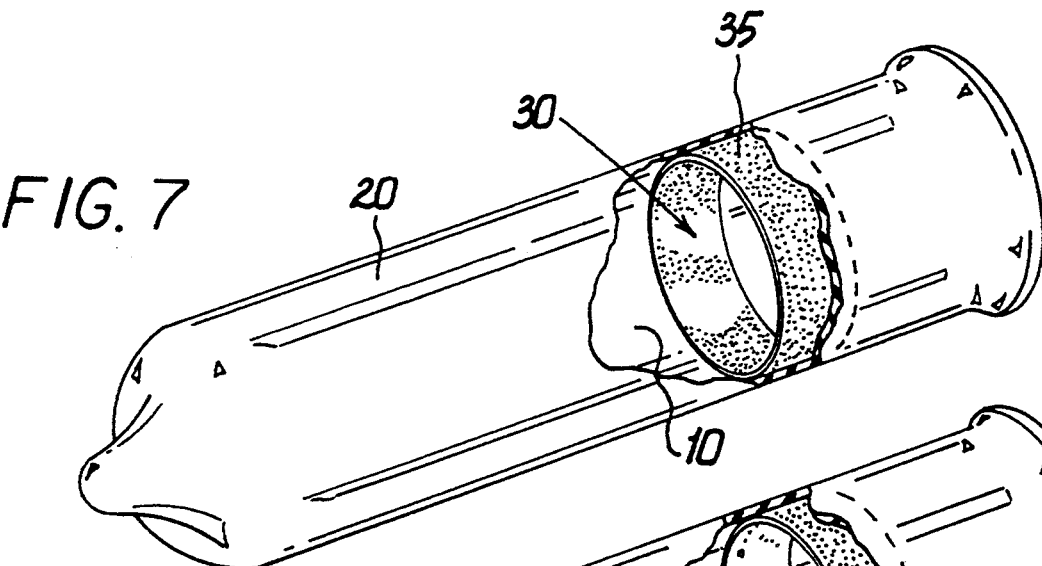
FIG. 7 is a perspective view of an annular embodiment of the present invention.

FIG. 7 shows a perspective view of a 3-layered transdermal patch configured as annular ring 35, but otherwise identical in structure and function to the 3-layered transdermal patch elsewhere described herein. Annular ring 35 is shown adhesively attached to inside surface 10 of a conventional condom.

Figure 8:
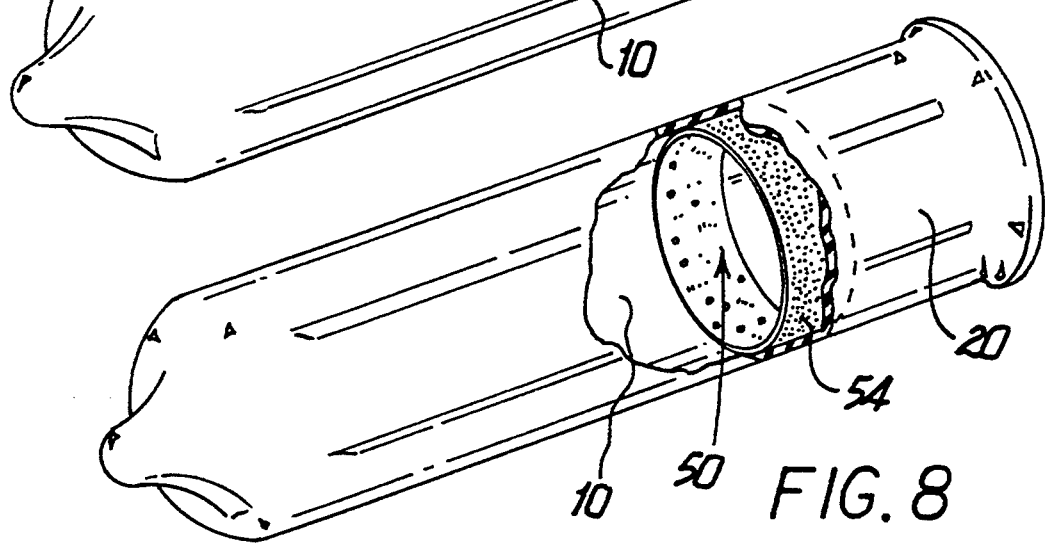
FIG. 8 is a perspective view of a further annular embodiment of the present invention.

FIG. 8 shows a perspective view of a 2-layered transdermal patch configured as annular ring 54, but otherwise identical in structure and function to the 2-layered transdermal patch elsewhere described herein. Annular ring 54 is shown adhesively attached to inside surface 10 of a conventional condom.

The present invention includes a male stimulating condom having a pharmaceutical vasodilator therein for producing and maintaining erection of the male sex organ during sexual intercourse. As shown in FIG. 1, there is provided a suitable flexible sheath having an inside portion with an inside surface 10 and an outside portion with an outside surface 20, and an open end 11 and a closed end 12.

An effective dose of a pharmaceutically suitable vasodilator is provided on the inside surface 10, so that the vasodilator penetrates the skin of the penis transdermally for producing and maintaining erection of the penis.

The dose of the vasodilator may be applied to the inside surface 10 of the condom during manufacture by spraying.

In this embodiment, the vasodilator of the condom is contained in a pharmaceutically suitable vehicle and is applied as a coating to the inside surface 10 of the condom for effective transdermal contact with the skin of the penis when the condom is applied thereto.

As shown in FIGS. 2–3a, in a preferred embodiment, the condom is provided with a suitably thin and flexible transdermal patch adhered to the inside of the condom. The transdermal patch 30 has at least one tapered edge 34, wherein the patch and tapered edge together present a substantially smooth profile. When in use, the patch and tapered edge produce substantially no friction or mechanical interference when the patch undergoes movement relative to an adjacent surface with which the patch is in slidable contact during sexual intercourse. In this embodiment, the transdermal patch 30 contains the vasodilator for dispensing to the skin of the penis when the condom is applied thereto.

As shown in FIG. 3, the transdermal patch 30 includes three substrate layers including an outer adhesive layer 31 for contact with and adhesive bonding to the inside surface of the condom, a middle layer 32 containing the vasodilator, and an inner adhesive layer 33 for contact with and adhesive bonding to the skin of the penis.

The middle layer 32 is capable of releasing the vasodilator for transdermal application to a male penis.

Moreover, the inner adhesive layer 33, for contact with and adhesively bonding to a penis, is capable of transmitting the vasodilator from middle layer 32 to the skin of a penis in contact with inner adhesive layer 33 during use of the condom.

Outer adhesive layer 31 provides a substantially weaker adhesive bonding to the condom inside surface 10. On the contrary, inner adhesive layer 33 provides a substantially stronger adhesive bonding to the skin of a penis, such that in use, the bonding of adhesive layer 33 to the skin of a penis results in release of the bond between outer adhesive layer 31 and condom inside surface 10. As a result transdermal patch 30 is released from attachment to the condom inside surface 10 and this releasing of the patch 30 permits the patch to move slidably relative to condom inside surface 10 as the penis skin surface moves in a normal, slidable motion relative to the condom during sexual intercourse.

The inner adhesive layer 33 is adhesively pressure sensitive. Adhesion of layer 33 to the penis skin surface is accomplished when the user manually applies pressure to the outside surface 20 of the condom in the area adjacent to transdermal patch 30. The application of manual pressure causes inner adhesive layer 33 to adhere to the penis skin surface.

The condom may preferably have outside surface 20 bearing a visual indicator of the location of transdermal patch 30, so that the user is able to apply manual pressure to the area of the visual indicator, in order to cause inner adhesive layer 33 to adhere to the penis skin surface.

As shown in FIGS. 4–6 the condom may alternatively be provided with a suitably thin and flexible transdermal patch adhered to the inside of the condom. The transdermal patch 50 contains the vasodilator for dispensing to the skin of the penis when the condom is applied thereto.

Moreover, the transdermal patch 50 has at least one tapered edge 33, so that the patch 50 and tapered edge 33 together present a substantially smooth profile and produce substantially no friction or mechanical interference when the patch undergoes movement relative to an adjacent surface with which the patch is in slidable contact, during sexual intercourse.

Transdermal patch 50 includes two substrate layers, as shown in FIG. 5, including an outer adhesive layer 51 for contact with and adhesive bonding to the inside surface of the condom, and a non-adhesive inner layer 52 containing the vasodilator. Inner layer 52 is capable of releasing the vasodilator into the skin of a penis.

The vasodilator transdermal patch may be sensitive to and be activated by mechanical pressure, so that the pressure sensitive transdermal patch thereby is adapted for dispensing the vasodilator in a discreet user controlled manner.

In this embodiment, the vasodilator is only released from transdermal patch 50 when the user applies manual pressure to the condom outside surface 20 in order to force the vasodilator by mechanical pressure to be released from inner layer 52.

When the inner layer 52 containing the vasodilator is in a form which is isolated from contact with the suitable pharmaceutical and lubricating vehicle. The contact between the vasodilator and the pharmaceutical and lubricating vehicle occurs only when the condom user applies mechanical pressure to condom outside surface 20 in an area adjacent to the vasodilator transdermal patch.

Preferably, the area occupied by transdermal patch 30 includes substantially less than one half of condom inner surface 10. In a preferred geometric design as shown in FIG. 7, the transdermal patch 30 includes an annular ring structure 35.

The area occupied by annular ring transdermal patch 35 may include substantially less than one half of condom inner surface 10.

The area occupied by transdermal patch 50 may include substantially less than one half of condom inner surface 10.

As shown in FIG. 8, the transdermal patch 50 preferably includes an annular ring structure 54.

The area occupied by annular ring transdermal patch 54 includes substantially less than one half of condom inner surface 10.

It is assumed that other modifications may be made to the present invention, without departing from the spirit and scope of the present invention, as noted in the appended claims.

I claim:

1. A male stimulating condom having a pharmaceutical vasodilator therein for producing and maintaining erection of the male sex organ during sexual intercourse, comprising:

a suitable flexible sheath having an inside with an inside surface and an outside with an outside surface, and an open end and a closed end;

an effective dose of pharmaceutically suitable vasodilator contained within the confines of a transdermal patch located on the inside of said condom, wherein the vasodilator penetrates the skin of the penis transdermally for producing and maintaining erection of the penis;

wherein the transdermal patch containing the vasodilator is applied to the inside surface of the condom during manufacture;

wherein the vasodilator is contained in a pharmaceutically suitable vehicle within said transdermal patch and said vasodilator is applied as a coating to the inside surface of said transdermal patch, said patch located within said condom for effective transdermal contact with the skin of the penis when the condom is applied thereto;

wherein said transdermal patch of said condom is a suitably thin and flexible transdermal patch adhered to the inside of said condom, said transdermal patch having at least one tapered edge, wherein said patch and tapered edge together present a substantially smooth profile and will produce substantially no friction or mechanical interference when said transdermal patch undergoes movement relative to an adjacent surface with which the patch is in slidable contact; and wherein said transdermal patch contains the vasodilator for dispensing to the skin of the penis when the condom is applied thereto;

wherein said transdermal patch comprises three substrate layers, including an outer adhesive layer for contact with and adhesive bonding to the inside surface of said condom, a middle layer containing said vasodilator, and an inner adhesive layer for contact with and adhesive bonding to the skin of the penis; wherein said middle layer is capable of releasing said vasodilator for transdermal application to a male penis; and said inner adhesive layer for contact with and adhesively bonding to a penis is capable of transmitting said vasodilator from said middle layer to the skin of a penis in contact with said inner adhesive layer during use of the condom; and further wherein said outer adhesive layer provides substantially weaker adhesive bonding to said inside surface of said condom and said inner adhesive layer provides a substantially stronger adhesive bonding to the skin of a penis, such that in use, the bonding of said inner adhesive layer to the skin of a penis results in release of the bond between said outer adhesive layer and said inside surface of said condom, thus releasing said transdermal patch from attachment to said inside surface of said condom and permitting said transdermal patch to move slidably relative to said inside surface of said condom as the penis skin surface moves in a normal, slidable motion relative to the condom during use.

2. The condom of claim 1 wherein said inner adhesive layer is adhesively pressure sensitive and wherein adhesion of said inner layer to the penis skin surface is accomplished when the user manually applies pressure to the outside surface of said condom in the area adjacent to said transdermal patch, wherein the manual pressure application causes said inner adhesive layer to adhere to the penis skin surface.

3. The condom of claim 2 wherein said outside surface of said condom bears a visual indicator of the location of said transdermal patch so that the user is able to apply manual pressure to the area of said visual indicator in order to cause said inner adhesive layer to adhere to the penis skin surface.

4. The condom of claim 3, wherein the area occupied by said transdermal patch comprises substantially less than one half of said inner surface of said condom.

5. The condom of claim 3, wherein said transdermal patch comprises an annular ring structure.

6. The condom of claim 5, wherein the area occupied by said annular ring transdermal patch comprises substantially less than one half of said inner surface of said condom.

* * * * *